United States Patent [19]

Jabalee

[11] 3,935,129

[45] Jan. 27, 1976

[54] LIQUID CLEANING COMPOSITIONS

[76] Inventor: Walter J. Jabalee, 44151 Lantern Lane, Apt. 1, Sterling Heights, Mich. 48077

[22] Filed: Oct. 25, 1973

[21] Appl. No.: 409,628

[52] U.S. Cl. .............. 252/525; 252/139; 252/153; 252/173; 252/529; 252/532; 252/540; 252/544; 252/548; 252/551; 252/559; 252/DIG. 13; 252/DIG. 14
[51] Int. Cl.² ........................................... C11D 3/08
[58] Field of Search............. 252/153, DIG. 13, 529, 252/DIG. 14, 525, 532, 540, 544, 548, 551, 559, 139, 173

[56] References Cited
UNITED STATES PATENTS

| | | | |
|---|---|---|---|
| 2,920,045 | 1/1960 | Hearn et al. ............. | 252/DIG. 14 X |
| 2,992,993 | 7/1961 | Pengilly ................... | 252/DIG. 14 X |
| 3,548,056 | 12/1970 | Eigen et al. ........................ | 252/153 |
| 3,553,138 | 1/1971 | Mace ................................... | 252/90 |
| 3,707,503 | 12/1972 | Kenny................................. | 252/117 |
| 3,812,041 | 5/1974 | Inamorato............................ | 252/89 |
| 3,812,042 | 5/1974 | Verdier....................... | 252/DIG. 14 |

OTHER PUBLICATIONS

*Cosmetics Science and Technology,* Edward Sagarin (Editor), Interscience Publishers, Inc., 1957, p. 405.

Primary Examiner—Leland A. Sebastian
Assistant Examiner—E. Suzanne Parr
Attorney, Agent, or Firm—Gifford, Chandler & Sheridan

[57] ABSTRACT

A "system" of aqueous liquid cleaning compositions is described wherein the concentrations of each of five basic ingredients — urea, glycerine, triethanolamine, an organic anionic detergent, and an organic nonionic detergent — are defined in terms of the concentration of alkali metal silicate. Within the system three preferred embodiments are used, by way of example, as a hair shampoo, a spot remover, and a laundry detergent, respectively.

19 Claims, 1 Drawing Figure

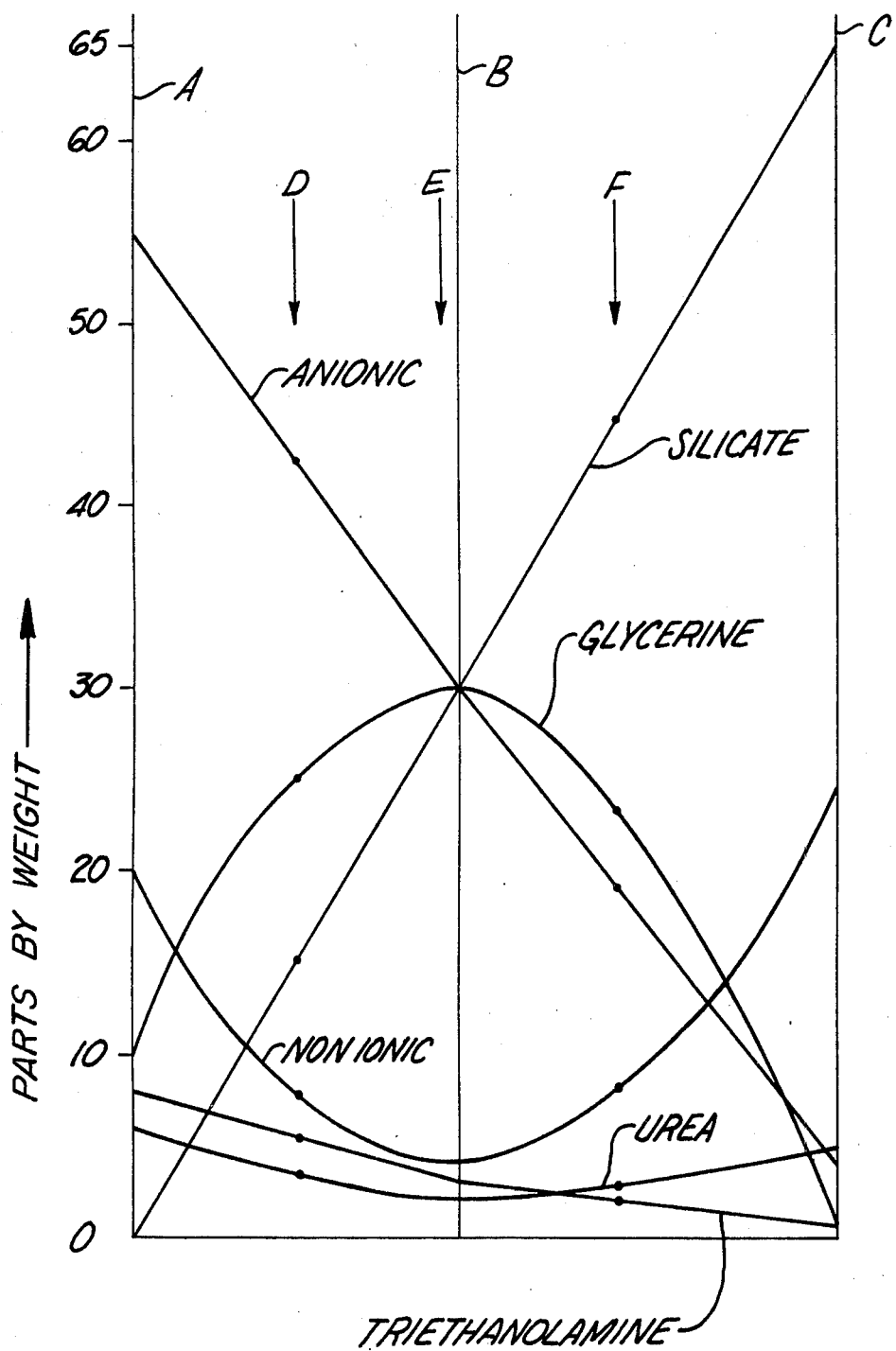

LIQUID CLEANING COMPOSITIONS

BACKGROUND OF THE INVENTION

There is now a large body of knowledge in the cleaning and detergent arts. It has become large partly because of the universal need to clean things and partly because of the many unique cleaning problems which have arisen. For example, soil on the surface of nonporous ceramic tile is generally much easier to remove than the same soil embedded in a highly porous fiber; a food stain in an evening gown has generally required a treatment quite different from that used to remove a crayon mark from a wall; and, to be extreme, a shampoo for human hair or a cleaner for human skin can usually be expected to be different from an oven cleaner.

The wide range of soils and stains and the large number of widely different sites in which they occur has been a factor in the "easy" solution to the problem where the "easy" solution might involve the use of an inflammable solvent, the use of a toxic solvent, or the use of phosphates or other ecologically unacceptable chemicals.

The differences in water hardness throughout the country has also posed a problem in the design of multipurpose cleaners.

There has been, therefore, a need for non-flammable, non-toxic, non-phosphate cleaners which can be used successfully with water of substantially any hardness. Secondly, there is a need for a cleaner "system"; that is, a group of chemicals which, by adjustment in accordance with a mathematical pattern form compositions which clean substantially any substrate of substantially any soil or stain. Thirdly, there is a need for such a cleaner system wherein all definable compositions are excellent cleaners and some are superior cleaners.

SUMMARY OF THE INVENTION

The above defined needs for a system of cleaners are met by the present invention. The compositions of the invention include five basic ingredients — urea, glycerine, triethanolamine, an organic anionic detergent, and an organic non-ionic anionic detergent — and one ingredient, an alkali metal silicate, which may or may not be present. The variation in concentrations of each of the ingredients within the system manifest a mathematical relationship which can be expressed in terms of the concentration of one of the ingredients, the alkali metal silicate.

It may be noted that the concentration of the alkali metal silicate is the reference concentration even though the silicate may be absent from the composition. As will appear hereinafter a zero concentration of an alkali metal silicate is just as significant a parameter as is any finite concentration.

In this connection the concentrations of two ingredients, the anionic detergent and the triethanolamine each are in approximately inverse proportion to the silicate concentration and the concentrations of three ingredients, the glycerine, urea, and non-ionic detergent, are approximately directly proportional to the silicate concentration over part of their concentration ranges and are approximately inversely proportional over the balance of their concentration ranges.

All concentrations herein are expressed in parts by weight. The term "non aqueous" components or ingredients refers to alkali metal silicate, urea, triethanolamine, glycerine, organic anionic detergents and organic non-ionic detergents.

The invention is defined as an aqueous liquid cleaning composition wherein the non-aqueous components comprise from zero to about 65 parts by weight of an alkali metal silicate and wherein the composition comprises the combination of (a) an anionic organic detergent and triethanolamine, the concentration of each of which is approximately inversely proportional to the concentration of said silicate in accordance with the following table:

|  |  | Parts by Weight | | |
| --- | --- | --- | --- | --- |
| Alkali metal silicate | about | 0 | 30 | 65 |
| Anionic detergent | about | 55 | 30 | 4 |
| Triethanolamine | about | 9 | 3 | 0.5 |
| Glycerine | about | 10 | 30 | 0.5 |
| Urea | about | 6 | 2 | 5 |
| Non-ionic detergent | about | 20 | 5 | 25 |

(b) glycerine, the concentration of which is approximately directly proportional to the concentration of said silicate between a silicate concentration of zero and about 30 and is approximately inversely proportional to the concentration of said silicate between a silicate concentration of about 30 and about 65 in accordance with said table, and (c) urea and a non-ionic organic detergent, the concentration of each of which is approximately inversely proportional to the concentration of said silicate at silicate concentrations between zero and about 30 and approximately directly proportional to the concentration of said silicate between silicate concentrations of about 30 to about 65 in accordance with said table.

A first preferred embodiment comprises about 55 parts of said anionic detergent, about 9 parts triethanolamine, about 10 parts glycerine, about 6 parts urea, and about 20 parts of said non-ionic detergent.

A second preferred embodiment comprises about 29 parts of an alkaline metal silicate, about 31 parts of said anionic detergent, about 3 parts triethanolamine, about 30 parts glycerine, about 2 parts urea, and about 5 parts of said non-ionic detergent.

A third preferred embodiment comprises about 65 parts of an alkali metal silicate, about 4 parts of said anionic detergent, about 0.5 parts triethanolamine, about 0.5 parts of glycerine, about 5 parts urea, and about 25 parts of said non-ionic detergent.

The mathematical relationship among the various ingredients of the compositions of the invention can be seen by reference to the accompanying drawing.

DESCRIPTION OF THE DRAWING

The single FIGURE illustrates the invention by means of a graph. In the graph the ordinate is parts by weight and spaced along the abcissa are three vertical lines, A, B and C, representing selected parameter compositions.

A line marked SILICATE is the concentration of alkali metal silicate present in various compositions and passes through zero on line A, through 30 on line B, and through 65 on line C.

A line marked ANIONIC is the total concentration of anionic organic detergents present in various compositions and passes through 55 on line A, through 30 on line B, and through 0.5 on line C.

A line marked GLYCERINE is the concentration of glycerine present in various compositions and passes through 10 on line A, through 30 on line B, and through 4 on line C. It may be noted that lines SILICATE, ANIONIC and GLYCERINE cross each other at about 30 parts by weight alkali metal silicate, about 30 parts by weight glycerine, and about 30 parts by weight anionic detergents.

A line marked NON-IONIC is the total concentration of organic non-ionic detergents in various compositions and passes through 20 on line A, through 5 on line B, and through 25 on line C.

A line marked TRIETHANOLAMINE is the concentration of triethanolamine in various compositions and passes through 8 on line A through 3 on line B and through 0.5 on line C.

A line marked UREA is the concentration of urea in various compositions and passes through 6 on line A, through 2 on line B, and through 5 on line C.

Because of a fortuitous characteristic of the six concentration curves on the graph, concentrations of alkali metal silicate of zero, 30 and 65 can serve as the parameters by which all other curves are determined.

Thus, as shown in the drawing, the anionic detergent concentration is approximately inversely proportional to the silicate concentration, line ANIONIC being defined by the fact that the concentrations of anionic detergent form a substantially straight line passing through 55 when SILICATE is at zero, through 30 when SILICATE is at 30, and through 4 when SILICATE is at 65. Similarly, concentrations of triethanolamine are approximately inversely proportional to silicate concentrations, line TRIETHANOLAMINE being defined by the fact that the concentrations of ethanolamine form a substantially straight line passing through 8 when SILICATE is at zero, through 3 when SILICATE is at 30, and at 0.5 when SILICATE is at 65.

As shown in the drawing, the concentration of glycerine is approximately directly proportional to the silicate concentration when the latter is between zero and 30, but is approximately inversely proportional to the silicate concentration when the latter is between 30 and 65; the concentrations of glycerine forming a curve which is convex upwardly and passes through 10 when SILICATE is at zero, through 30 when SILICATE is at 30, and through 0.5 when SILICATE is at 65.

As shown in the drawing the concentrations of urea and the concentrations of non-ionic detergents each are substantially inversely proportional to the silicate concentration when the latter is between zero and 30, but are approximately directly proportional to the silicate concentration when the latter is between 30 and 65; the concentrations of each forming curves which are concave upwardly. As shown, line NON-IONIC passes through 20 when SILICATE is at zero, through 5 when SILICATE is at 30, and through 25 when SILICATE is at 65. Further as shown, line UREA passes through 8 when SILICATE is at zero, through 2 when SILICATE is at 30, and through 5 when SILICATE is at 65.

In the drawing arrow D represents an intermediate composition between two preferred compositions (line A and arrow E) while arrow F represents an intermediate composition between two preferred compositions (arrow E and line C). Thus, A, E, and C are preferred compositions; D and F are intermediate compositions selected to illustrate the nature of compositions lying in the system between preferred compositions; and B is a unique composition selected because it is a parameter by which the system of compositions can be defined.

The term "an organic anionic detergent" means one, two, or more than two organic anionic detergents. There are numerous such anionic detergents known to the art. They are generally a sulfate or sulphonate having a hydrophobic substituent.

Examples of suitable anionic detergents are: (a) sulfuric acid esters of polyhydric alcohols incompletely esterified with higher fatty acids such as coconut oil monoglyceride monosulfate and tallow diglyceride monosulfate; (b) long chain pure or mixed alkyl sulfates such as lauryl sulfate, cetyl sulfate, and higher fatty alcohol sulfates derived from coconut oil; (c) the hydroxy sulfonated higher fatty esters such as the higher fatty acid esters of 2, 3 - dihydroxypropane sulfonic acid; (d) the higher fatty acid esters of low molecular weight alkylol sulfonic acids, such as the oleic acid ester of isethionic acid; (e) the sulfated higher fatty acid alkylol-amides such as ethanolamide sulfates and the higher fatty acid amides of amine alkyl sulfonic acids such as the lauric amids of taurine; (f) sulfonic acid salts of alkylated aromatic hydrocarbon compounds having an alkyl substituent wherein the aromatic portion of the molecule may be mono- or polynuclear; e.g., benzene, toluene, xylene, naphthalene, phenanthrene, anthracene, etc. and may contain other substituents such as hydroxyl groups or short chain alkyl groups such as in phenol, cresol, phenol ethers, toluene, xylene, etc; and wherein the long chain alkyl substituent of the alkylated aromatic molecule preferably is saturated and may be straight chain or branched; e.g. dodecyl, hexyl, octyl, nonyl, and decyl groups as well as mixed alkyls derived from fatty materials, cracked paraffins or polymers of lower mono olefins, etc.

The anionic detergents may be used in the form of their sodium, potassium, lithium, ammonium, triethanolamine, etc. salts.

Referring to anionic detergents, I have found that best results are obtained using a mixture of dodecyl benzene sulfonic acid and a coconut fatty alcohol ether sulfate at concentrations, respectively, of about 50 and 5 when the silicate concentration is zero, about 28 and 2 when the silicate concentration is about 30, and about 2 and 2 when the silicate concentration is about 65.

Similarly the term "a non-ionic organic detergent" means one, two, or more than two non-ionic organic detergents. There are numerous such non-ionic detergents known to the art. They are generally lower alkylene oxide condensation products of hydrophobic compounds.

Examples of suitable non-ionic detergents are:

a. ethylene oxide, propylene oxide, and butylene oxide condensation products with higher fatty acids, higher fatty alcohols, or alkylated aromatic hydrocarbons;

b. polypropylene glycols having a molecular weight greater than 900;

c. amide and amine condensates such as fatty acid alkylol amides (e.g. N-bis (2-hydroxy-ethyl) -lauramide).

d. condensation products of fatty acid chlorides with hydrolysed natural protein (lysalbinic acid derivatives).

Referring to non-ionic detergents, I have found that best results are obtained using a mixture of isooctyl phenol polyethylene glycol ether and a coconut fatty acid alkylol amide at concentrations, respectively, of about 13 and 7 when the concentration of silicate is zero, about 2 and 2 when the concentration of silicate is about 30, about 21 and 4 when the concentration of silicate is about 65.

Other detergents; as well as stabilizers, defoamers, brighteners and other adjuvants; can be added where desired. Similarly, the pH can be varied depending on the use to which the selected composition is to be put.

EXAMPLE 1

The following composition, representing the preferred composition of line A of the drawing, was prepared:

| Ingredient | Parts by Weight |
| --- | --- |
| urea | 6 |
| triethanolamine | 9 |
| glycerine | 10 |
| dodecylbenzene sulfonic acid | 50 |
| coconut fatty alcohol ether sulfate | 5 |
| isooctyl phenol polyethylene glycol ether | 13 |
| coconut fatty acid alkylol amide | 7 |
| Total (non aqueous) | 100 |
| water | 250 |
| pH adjusted to | 7.5 |

The composition of Example 1 is particularly valuable as a hair shampoo. At near neutral pH values it has a wet out time of 9.5 – 12.5 seconds, as compared to the wetting out times of the two leading commercially available shampoos of 30.5 and 70 seconds respectfully. In addition, it has proved to be less irritating to the eyes than said two leading shampoos.

The composition was tested as a shampoo for human hair by a number of professional hair dressers who compared it with those available commercial products which each had previously considered best. It was their opinion that the above composition of the invention was superior to any other tested. The following advantages were cited:

1. The rapid rinse out.
2. Only one application of the test composition was required whereas normally two applications of commercially available shampoos are required.
3. Deep cleaning of the scalp was achieved resulting in a good control of dandruff.
4. There was no static electricity in the shampooed hair.
5. No conditioners or special rinses were required in about 90 percent of the cases to enable a satisfactory brushing out of the hair.

The composition also is an excellent cleaner for the human body; for dishes, especially for glassware; for rugs, and can be used as a detergent additive to other cleaners in place of the usual organic detergents of commerce.

The composition of Example 1 is particularly useful over a pH range of about 6 – 8.5.

EXAMPLE 2

The following composition, representing the preferred composition of arrow E of the drawing, was prepared:

| Ingredient | Parts by Weight |
| --- | --- |
| sodium silicate | 29 |
| urea | 2 |
| triethanolamine | 3 |
| glycerine | 30 |
| dodecyl benzene sulfonic acid | 29 |
| coconut fatty alcohol ether sulfate | 2 |
| isooctyl phenol polyethylene glycol ether | 3 |
| coconut fatty acid alkylol amide | 2 |
| Total (non aqueous) | 100 |
| water | 1500 |
| pH adjusted to | 12 |

The composition of Example 2 was tested as an all purpose spot remover against the commercially available spot removers previously considered as the best available. The above composition proved superior in over all cleaning to all tested. This superiority of this composition is especially noteworthy for the reason that the most successful spot removers to date have included ecologically unacceptable organic solvents. The only disadvantage of the composition is that it is slower in its attack on hydrocarbon oils and greases than the solvent type cleaners but yet cleans such oil and grease stains.

The composition of Example 2 is excellent as a spot remover of a wide range of foods and soils and is uniquely superior as a hard surface cleaner. It serves, for example, as an oven cleaner, a wall cleaner, and for the removal of spots from rugs, tile, wood, and various fabrics. It has found application in the removal of stains set in by other cleaners and for the removal of water rings from fabrics where a stain had been "dabbed" with water. The composition is surprisingly mild for a high pH cleaner for a reason which is not yet apparent.

EXAMPLE 3

The following compositions, representing the preferred composition of line C of the drawing, was prepared:

| Ingredient | Parts by Weight |
| --- | --- |
| sodium silicate | 65 |
| urea | 5 |
| triethanolamine | 0.5 |
| glycerine | 0.5 |
| dodecyl benzene sulfonic acid | 2 |
| coconut fatty alcohol ether sulfate | 2 |
| isooctyl phenol polyethylene glycol ether | 21 |
| coconut fatty acid alkylol amide | 4 |
| Total (non aqueous) | 100 |
| water | 250 |
| pH adjusted to | 13 plus |

The composition was tested as a laundry detergent and was tested against several commercially available liquid laundry detergents previously considered as the best available. The most noteworthy result of the comparison, in addition to its generally superior performance, was the results obtained with the composition with difficultly removable stains like grape juice and mustard stains. For example, whereas the best of the commercially available liquid detergents turned a dark blue grape juice stain into a light gray stain, the composition of Example 3 removed the stain completely.

EXAMPLE 4

The following composition, representing the composition of arrow D of the drawing, was prepared:

| Ingredient | Parts by Weight |
| --- | --- |
| sodium silicate | 15 |
| urea | 3 |
| triethanolamine | 7 |
| glycerine | 25 |
| dodecyl benzene sulfonic acid | 39 |
| coconut fatty alcohol ether sulfate | 3 |
| isooctyl phenol polyethylene glycol ether | 5 |
| coconut fatty acid alkylol amide | 3 |
| | 100 |
| water, various compositions in range | 250–1500 |
| pH, adjusted for various samples to range | 7–12 |

The composition of Example 4 was tested in a manner similar to the compositions of Example 1 and 2. Although it was not as good as the latter compositions it proved to be at least equal to the commercially available cleaners used in the comparison. By way of example, the composition of Example 4 tends to leave a film on glassware but continues to be a superior rug cleaner.

EXAMPLE 5

The following composition, representing the composition of arrow f of the drawing, was prepared:

| Ingredient | Parts by Weight |
| --- | --- |
| sodium silicate | 45 |
| urea | 3 |
| triethanolamine | 2 |
| glycerine | 23 |
| dodecyl benzene sulfonic acid | 17 |
| coconut fatty alcohol ether sulfate | 2 |
| isooctyl phenol polyethylene glycol ether | 5 |
| coconut fatty acid alkylol amide | 3 |
| | 100 |
| water, various compositions in range | 250 – 1500 |
| pH, adjusted for various samples in range | 12 – 13.5 |

The composition of Example 5 was tested in a manner similar to Examples 2 and 3. Although it was not as good as the latter compositions it proved to be at least equal to the commercially available cleaners used in the comparison. By way of example, the composition of Example 5 was equal to, but not superior to, the leading commercially available liquid laundry detergent in removing grape juice stains from cotton fabrics but yet was a better all purpose cleaner than any of the tested commercially available cleaners.

The pH adjustments in the examples were made in the alkaline direction with sodium or potassium hydroxide. Adjustments in the acid direction were made by the use of predetermined mixtures of dodecyl benzene sulfonic acid and salts thereof.

The preferred alkali metal silicates are sodium and potassium silicates and preferably, water glass.

The degree of dilution of each of the compositions of the invention can be quite variable. Generally the composition is packaged in a relatively concentrated form to be diluted by the user in accordance with the use intended. A spot remover (e.g. Example 2) is generally used in its original dilution; a shampoo (e.g. Example 1) is generally diluted with at least the water used to wet the hair prior to applying the shampoo, and a laundry cleaner (e.g. Example 3) is generally diluted many fold.

It is usually taken for granted that one skilled in the art can design a specific cleaner for a specific cleaning job and that, because there are so many types of soils and stains in so many types of sites, that one so skilled would come up with a wide variety of cleaners for all such jobs. It follows then that an all purpose cleaner would of necessity be expected to be a compromise, doing nothing well. The presently designed system, however, is therefore surprising in that it is in no sense a compromise. It does substantially every cleaning job well and many in a superior manner.

I claim:

1. An aqueous detergent composition comprising zero to about 65 parts by weight of an alkali metal silicate and a combination of an anionic organic detergent, a non-ionic organic detergent, triethanolamine, glycerine, and urea; each in an approximate proportion relative to the proportion of said silicate as indicated in the drawing.

2. The composition as defined in claim 1 and comprising about 55 parts of said anionic deterggent, about 9 parts triethanolamine, about 10 parts glycerine, about 6 parts urea, and about 20 parts of said non-ionic detergent.

3. The composition as defined in claim 2 where said anionic detergent is about 50 parts dodecy, benzene sulfonic acid and about 5 parts of a coconut fatty alcohol ether sulfate.

4. The composition as defined in claim 2 where said non-ionic detergent is about 13 parts isooctyl phenol polyethylene glycol ether and about 7 parts of a coconut fatty acid alkylol amide.

5. The composition as defined in claim 1 and comprising about 9 parts triethanolamine, about 10 parts glycerine, about 6 parts urea, about 50 parts dodecyl benzene sulfonic acid, about 5 parts of a coconut fatty alcohol ether sulfate, about 13 parts isooctyl phenol polyethylene glycol ether, and about 7 parts of a coconut fatty acid alkylol amide.

6. The composition as defined in claim 2, wherein said water proportion is about 250 parts.

7. The composition is defined claim 2 and having a pH of about 6 –8.5.

8. The composition as defined in claim 1 and comprising about 29 parts of an alkali metal silicate, about 31 parts of said anionic detergent, about 3 parts triethanolamine, about 30 parts glycerine, about 2 parts urea, and about 5 parts of said non-ionic detergent.

9. The composition as defined in claim 8 where said anionic detergent is about 29 parts dodecyl benzene sulfonic acid and about 2 parts of a coconut fatty alcohol ether sulfate.

10. The composition as defined in claim 8 where said non-ionic detergent is about 3 parts isooctyl phenol polyethylene glycol ether and about 2 parts of a coconut fatty acid alkylol amide.

11. The composition as defined claim 1 and comprising about 29 parts of an alkali metal silicate, about 3 parts triethanolamine, about 30 parts glycerine, about 2 parts urea, about 29 parts dodecyl benzene sulfonic acid, about 2 parts of a coconut fatty alcohol ether sulfate, about 3 parts isooctyl phenol polyethylene glycol ether, and 2 parts of a coconut fatty acid alkylol amide.

12. The composition as defined claim 8 where said water proportion is about 1500 parts.

13. The composition as defined in claim 8 and having a pH above about 11.

14. The composition as defined in claim 1 and comprising about 65 parts of an alkali metal silicate, about 4 parts of said anionic detergent, about 0.5 parts triethanolamine, about 0.5 parts glycerine, about 5 parts urea, and about 25 parts of said non-ionic detergent.

15. The composition as defined in claim 14 where said anionic detergent is about 2 parts dodecyl benzene sulfonic acid and about 2 parts of a coconut fatty alcohol ether sulfate.

16. The composition as defined in claim 14 where said non-ionic detergent is about 21 parts isooctyl phenol polyethylene glycol ether and about 4 parts of a coconut fatty acid alkylol amide.

17. The composition as defined in claim 1 and comprising about 65 parts of an alkali metal silicate, about 0.5 parts triethanolamine, about 0.5 parts glycerine, about 5 parts urea, about 2 parts dodecyl benzene sulfonic acid, about 2 parts of a coconut fatty alcohol ether sulfate, about 21 parts isooctyl phenol polyethylene glycol ether, and about 4 parts of a coconut fatty acid alkylol amide.

18. The composition as defined in claim 14 where said water proportion is about 250 parts.

19. The composition as defined in claim 14 and having a pH above about 12.

* * * * *